United States Patent
Becker et al.

(10) Patent No.: US 11,931,109 B2
(45) Date of Patent: Mar. 19, 2024

(54) INTERACTIVE PLANNER FOR REPAIR OR REPLACEMENT SURGERY

(71) Applicant: DasiSimulations LLC, Dublin, OH (US)

(72) Inventors: Taylor Nicole Becker, Rancho Palos Verdes, CA (US); Breandan Yeats, Columbus, OH (US); Robert Gerdisch, Seattle, WA (US); Lakshmi Prasad Dasi, Dublin, OH (US)

(73) Assignee: DASISIMULATIONS, LLC, Dublin, OH (US)

( * ) Notice: Subject to any disclaimer, the term of this patent is extended or adjusted under 35 U.S.C. 154(b) by 0 days.

(21) Appl. No.: 18/450,231

(22) Filed: Aug. 15, 2023

(65) Prior Publication Data

US 2024/0050157 A1 Feb. 15, 2024

Related U.S. Application Data

(60) Provisional application No. 63/371,444, filed on Aug. 15, 2022.

(51) Int. Cl.
*A61B 34/10* (2016.01)
*A61B 34/00* (2016.01)
*G06T 17/20* (2006.01)

(52) U.S. Cl.
CPC .............. *A61B 34/10* (2016.02); *A61B 34/25* (2016.02); *G06T 17/20* (2013.01); *A61B 2034/104* (2016.02); *A61B 2034/105* (2016.02); *A61B 2034/107* (2016.02); *G06T 2207/30048* (2013.01); *G06T 2210/41* (2013.01)

(58) Field of Classification Search
CPC ... A61B 34/10; A61B 34/25; A61B 2034/104; A61B 2034/105; A61B 2034/107; G06T 17/20; G06T 2207/30048; G06T 2210/41
See application file for complete search history.

(56) References Cited

U.S. PATENT DOCUMENTS

| | | | |
|---|---|---|---|
| 10,178,157 B2 | 1/2019 | Avisar | |
| 2009/0311655 A1* | 12/2009 | Karkanias | G09B 5/065 434/262 |
| 2015/0112659 A1* | 4/2015 | Mortier | A61B 34/10 703/11 |
| 2018/0098814 A1* | 4/2018 | Avisar | G16H 20/40 |

(Continued)

OTHER PUBLICATIONS

Hou et al. "A new model of soft tissue with constraints for interactive surgical simulation." Computer Methods and Programs in Biomedicine 175 (2019): 35-43. (Year: 2019).*

(Continued)

*Primary Examiner* — Katrina R Fujita
(74) *Attorney, Agent, or Firm* — BENESCH, FRIEDLANDER, COPLAN & ARONOFF LLP

(57) ABSTRACT

In certain aspects of the present disclosure, a computer-implemented method includes receiving a 3D imaging. The method includes generating 3D models based on the 3D imaging. The method includes generating, responsive to a pre-determined set of surgical steps, a finite number of 4D time deformation scenes for each pre-determined surgical step associated with the 3D models. The method includes displaying selectively interactive simulations based on the finite number of 4D time deformation scenes. Systems and machine-readable media are also provided.

20 Claims, 14 Drawing Sheets

(56) References Cited

U.S. PATENT DOCUMENTS

| | | | |
|---|---|---|---|
| 2018/0168730 A1* | 6/2018 | Nazy | G16H 30/40 |
| 2019/0298450 A1* | 10/2019 | Dasi | G16H 50/50 |
| 2019/0328458 A1* | 10/2019 | Shmayahu | A61B 5/064 |
| 2020/0170709 A1* | 6/2020 | Wissel | G16H 20/40 |
| 2021/0259776 A1* | 8/2021 | Upadrasta | G16H 50/50 |
| 2023/0293236 A1* | 9/2023 | Wright | G16H 50/50 |
| | | | 600/424 |

OTHER PUBLICATIONS

Romarowski et al. "A novel computational framework to predict patient-specific hemodynamics after TEVAR: integration of structural and fluid-dynamics analysis by image elaboration." Computers & Fluids 179 (2019): 806-819. (Year: 2019).*

Cardiovascular diseases affect nearly half of American adults, statistics show. American Heart Association. Jan. 31, 2019. Accessed Nov. 13, 2023. https://www.heart.org/en/news/2019/01/31/cardiovascular-diseases-affect-nearly-half-of-american-adults-statistics-show.

Chang CC, Veen KM, Hahn RT, Bogers A, Latib A, Oei F, Abdelghania M, Modolo R, Ho SY, Abdel-Wahab M, Bosmans J, Caliskan K, Taramasso M, Serruys PW, Bax JJ, Meigham N, Takkenberg JM, Lurz P, Modlne T, Soliman 0. Uncertainties and challenges in surgical and transcatheter tricuspid valve therapy: A state-of-the-art expert review. Eurooean Heart Journal. 2020;41(20): 1932-1940.

* cited by examiner

INTERACTIVE PLANNER FOR REPAIR OR REPLACEMENT SURGERY

CROSS-REFERENCE TO RELATED APPLICATIONS

The present application claims the benefit of priority under 35 U.S.C. § 119 from U.S. Provisional Patent Application No. 63/371,444 entitled "Interactive Planner for Repair or Replacement Surgery," filed on Aug. 15, 2022, the disclosure of which is hereby incorporated by reference in its entirety for all purposes.

TECHNICAL FIELD

The present specification generally relates to integrated surgical simulations, and more specifically relates to integrated surgical simulations with interactive planner for repair or replacement surgery.

BACKGROUND

Structural heart disease (SHD) intervention is growing at the fastest rate in cardiology and cardiac surgery. Each year, new procedures and devices are developed and introduced. These interventions include, for example, aortic valve, mitral valve, atrial septal, ventricular septal, left atrial appendage occlusion, tricuspid valve, and pulmonary valve interventions.

Heart disease is the leading cause of death in the United States. As of 2019, it was estimated that around 48% of Americans have cardiovascular disease. Heart surgery has become more advanced within the last 15 years, especially with the development of Transcatheter Heart Valve Replacement (THVR) procedures and surgical Heart Valve Repair procedures.

In some scenarios, Hospital Heart Teams will meet regularly to determine the course of treatment for their heart valve patients. These patients may undergo a variety of treatments, including heart valve replacement or heart valve repair. While there are patient populations ideal for each treatment respectively, there is a third population of patients that are candidates for either a repair or a replacement. To date, there has not been a randomized prospective trial to definitively conclude which course of treatment is the most appropriate for this subset of patients. Thus, there is a need for physicians to visualize the outcomes of a repair versus a replacement in a patient specific manner when deciding the course of treatment for these patients. While both replacement and repair procedures are valid treatment options for some patients, they each have their own set of potential complications and treatment efficacies that physicians must objectively analyze.

There is growing evidence that valve related complications, such as leaflet thrombosis, prosthesis mismatch, and coronary ostia obstruction, and leaks, are highly correlated to the interaction of the transcatheter heart valve (THV) device with the patient's individual anatomical structure and the ensuing flow dynamics, costing hospitals, and sometimes even declining patient care in certain circumstances, when there is high uncertainty about potential complications. With respect to surgical repairs (e.g., valve repair, congenital defect repair, etc.), there exists very limited simulation techniques available for preoperative planning.

The description provided in the background section should not be assumed to be prior art merely because it is mentioned in or associated with the background section. The background section may include information that describes one or more aspects of the subject technology.

SUMMARY

According to certain aspects of the disclosed technology, systems and methods are provided for pre-operatively planning medical surgical repair or implantation procedure, such as, but not limited to structural heart procedures. The disclosed technology allows a physician to have multiple integrated simulations to, for example, navigate between multiple structural heart procedures in order to visualize a simulated prediction of the long-term functionality of the heart structures, which may be in need of surgical intervention. The disclosed technology distinguishes itself from others of its kind by interpolating between simulated outputs that are generated off-time, enabling the physician to visualize changes in simulated outcomes in real-time as continuous reactions to changes in initial parameters. This feature is important for a user to experience real-time free surgical exploration with real-time feedback on functional efficacy of the repair or implant configuration.

According to certain aspects of the present disclosure, a computer-implemented method includes receiving 3D imaging data. The method includes generating 3D models based on the 3D imaging. The method includes generating, responsive to a pre-determined set of surgical steps, a finite number of 4D time deformation scenes for each pre-determined surgical step associated with the 3D models. The method includes displaying selectively interactive simulations based on the finite number of 4D time deformation scenes.

According to other aspects of the present disclosure, a system is provided. The system includes a memory including instructions and a processor configured to execute the instructions which, when executed, cause the processor to receive a 3D imaging. The processor is configured to execute the instructions which, when executed, cause the processor to generate 3D models based on the 3D imaging. The processor is configured to execute the instructions which, when executed, cause the processor to generate, responsive to a pre-determined set of surgical steps, a finite number of 4D time deformation scenes for each pre-determined surgical step associated with the 3D models. The processor is configured to execute the instructions which, when executed, cause the processor to display selectively interactive simulations based on the finite number of 4D time deformation scenes.

According to other aspects of the present disclosure, a non-transitory machine-readable storage medium comprising machine-readable instructions for causing a processor to execute a method is provided. The method includes generating 3D models based on the 3D imaging. The method includes generating, responsive to a pre-determined set of surgical steps, a finite number of 4D time deformation scenes for each pre-determined surgical step associated with the 3D models. The method includes displaying selectively interactive simulations based on the finite number of 4D time deformation scenes.

According to other aspects of the present disclosure, a method of real-time interactive navigation smoothly between different surgical repair or device implant scenarios or configurations is provided.

According to other aspects of the present disclosure, a method for the visualization of the changed physical properties of tissue deformation integrated into the simulation is provided.

According to other aspects of the present disclosure, a method visualizing how surrounding structural heart tissues will heal over time, after the structural heart procedure is provided.

According to other aspects of the present disclosure, a method for visualizing how the healing of structural heart tissues after structural heart procedures alters the function of the heart over time is provided.

According to other aspects of the present disclosure, a method for measuring changes in valve deployment depth, angle, and off centered deployment for further procedure optimization is provided.

According to other aspects of the present disclosure, a method for simulation of structural heart tissue manipulation and simulation of resulting tissue function is provided.

According to other aspects of the present disclosure, a method for real time interactive visualization and manipulation of various structural heart procedures (congenital heart defects, valve replacement, valve repair) is provided.

According to other aspects of the present disclosure, a method for the visualization of various bail-out strategies during structural heart surgery when indicated is provided.

According to other aspects of the present disclosure, a method for integrating physical properties of cardiac tissue into deep learning artificial neural network algorithm is provided.

According to other aspects of the present disclosure, a method for training database of structural heart procedures for the purpose of identifying new tissue interactions and potential procedural complications is provided.

According to other aspects of the present disclosure, a method allowing for the digital measurement of structural heart components to aid in the planning of cardiac surgeries and transcatheter procedures is provided.

According to other aspects of the present disclosure, a method for training the database on the healing/remodeling of specific cardiac tissues that are the focus of surgical or transcatheter intervention is provided.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

Figure 1:
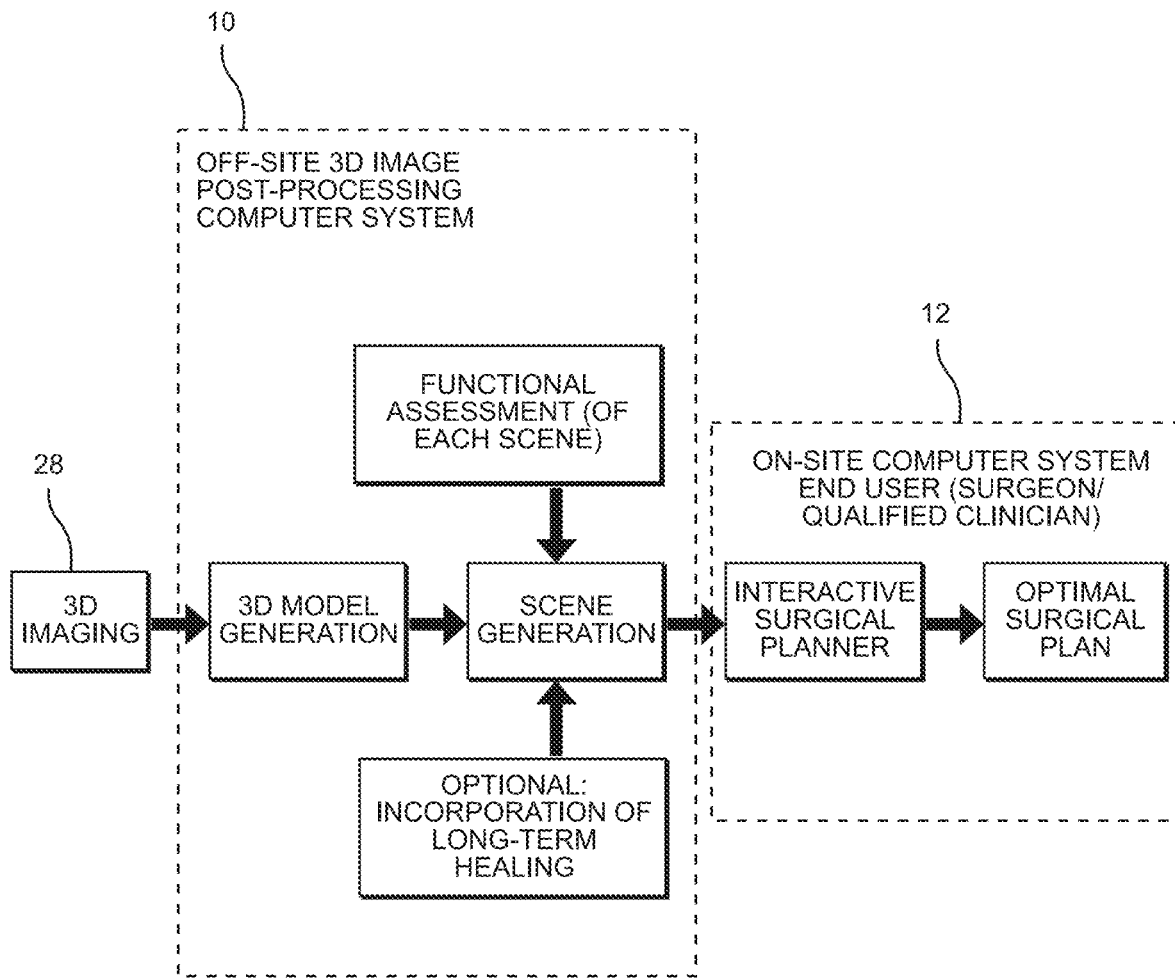
FIG. 1 illustrates an example architecture for generating integrated interactive simulations of a 3D image.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various ways, all without departing from the scope of the present disclosure. Accordingly, the drawings and description are to be regarded as illustrative in nature and not restrictive.

According to certain aspects of the disclosed technology, systems and methods are provided for pre-operatively planning medical surgical repair or implantation procedure, such as, but not limited to structural heart procedures. The disclosed technology allows a physician to have multiple integrated simulations to, for example, navigate between multiple structural heart procedures to visualize a simulated prediction of the long-term functionality of the heart structures, which may require surgical intervention. The disclosed technology distinguishes itself from others of its kind by interpolating between simulated outputs that are generated off-time, enabling the physician to visualize changes in simulated outcomes in real-time as continuous reactions to changes in initial parameters. This feature is important for a user to experience real-time free surgical exploration with real-time feedback on functional efficacy of the repair or implant configuration.

In certain aspects, the disclosed technology allows for the (1) optimization of patient outcomes by bringing expert biomechanically optimized strategies for valve selection and deployment guidance including risk mitigation strategies to all heart teams and (b) saving hospital time and money with the increasing push from "fee for service" to a "pay for performance" health care reimbursement environment.

While the disclosed technology is applicable to any medical surgical repair or implantation procedure, an exemplarily description in the context of structural heart surgery will follow. The field of structural heart interventions is a vast and rapidly evolving medical specialty. Thus, it is imperative that surgeons and interventional cardiologists/ imagers can visualize the simulations of various procedures in a patient specific manner.

The disclosed technology includes a simulation component of a computational model that allows physicians to visualize bio-physics based cardiac tissue interactions in various structural heart procedures. A deep learning algorithm of the disclosed technology accounts for or models the pre- and post-procedural biomechanics of cardiac structures and quantitatively assesses the function of the diseased anatomy pre- and post-procedurally for both valve replacements and valve repairs. The biomechanical properties of tissue were derived from preoperative CT (computed tomography) imaging by solving an inverse problem to fit the reduced order model parameters through deep learning applied to a dataset of pre-procedural and post-procedural imaging (comprising clinical patient databases and bench experiments) and then incorporated into the deep learning algorithm. Additionally, the disclosed technology takes into consideration how the tissue being manipulated in the procedure will heal and change over time. This may also be considered a fifth dimension. This will allow physicians to have a better understanding of the long-term physiological functioning of the intervention, rather than a simulation of the acute surgical procedure alone. This physiological functioning will consider tissue restructuring after the intervention, as well as hemodynamic variability, contingent on the procedure performed. The material properties used to generate the simulations will be trained from multi-phase CT scans or other imaging modalities such as MRI (magnetic resonance imaging), Ultrasound, PET (positron emission tomography), Nuclear or other functional imaging modalities, because they contain information regarding the structure-function relationship of a particular structural heart disease state.

FIG. 1 illustrates an example architecture 100 for generating integrated interactive simulations of a 3D image. For example, the architecture 100 includes a server 10 and a user device 12 connected over a network 14.

The server 10 can be any device having an appropriate processor, memory, and communications capability for communicating with the user device 12. For purposes of load balancing, the server 10 may include multiple servers. The user device 12, to which the server 10 communicates with over the network 14, can be, for example, a tablet computer, a mobile phone, a mobile computer, a laptop computer, a portable media player, an electronic book (eBook) reader, or any other device having appropriate processor, memory, and communications capabilities. In certain aspects, the server 10 can be a cloud computing server of an infrastructure-as-a-service (IaaS) and be able to support a platform-as-a-service (PaaS) and software-as-a-service (SaaS) services.

The network 14 can include, for example, any one or more of a personal area network (PAN), a local area network (LAN), a campus area network (CAN), a metropolitan area network (MAN), a wide area network (WAN), a broadband network (BBN), the Internet, and the like. Further, the network 14 can include, but is not limited to, any one or more of the following network topologies, including a bus network, a star network, a ring network, a mesh network, a star-bus network, tree or hierarchical network, and the like.

Figure 2:
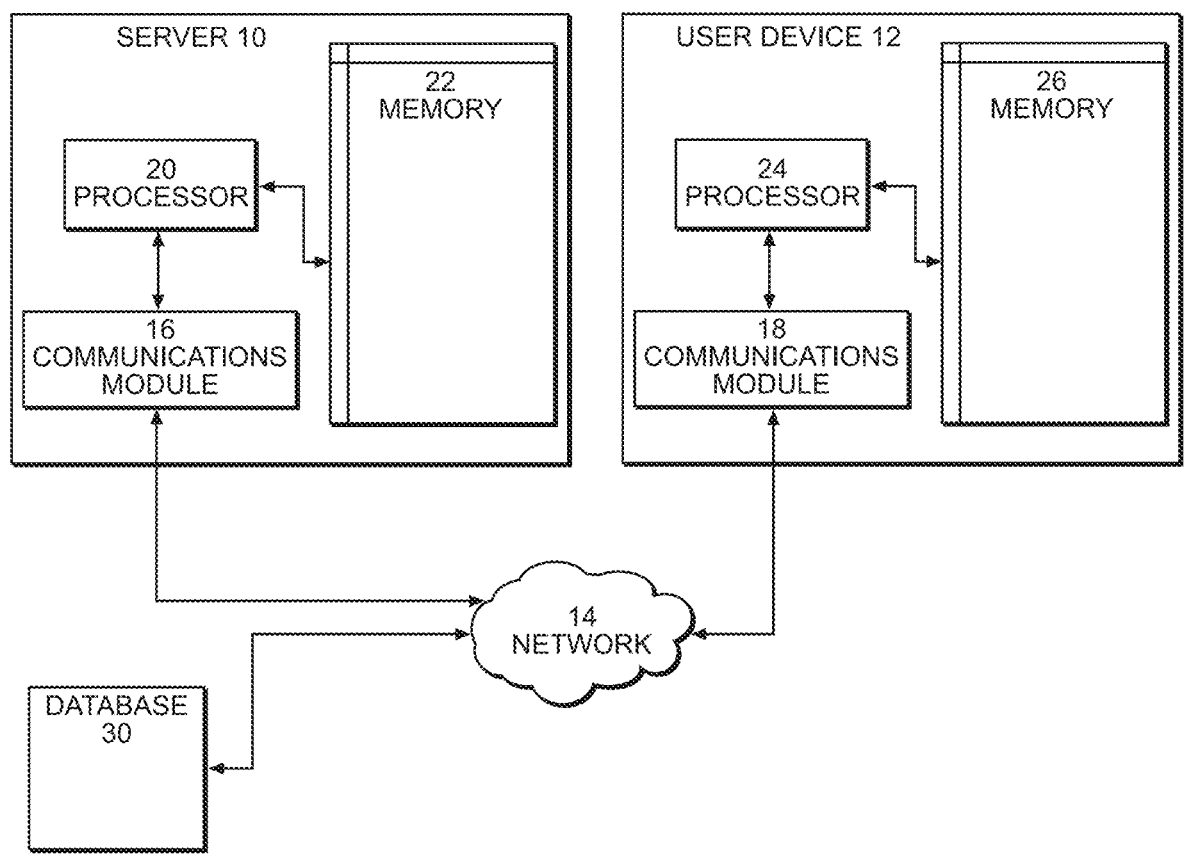
FIG. 2 is an example block diagram of a server and a user device according to certain aspects of the disclosure.

FIG. 2 is a block diagram illustrating examples of the server 10 and the user device 12 in the architecture of FIG. 1 according to certain aspects of the disclosure. It should be understood that for purposes of explanation the user device 12 is described, but any number of the user device 12 could be used.

The server 10 and the user device 12 are connected over the network 14 via respective communication modules 16, 18. The communication modules 16, 18 are configured to interface with the network 14 to send and receive information, such as data, requests, responses, and commands to other devices on the network 14. The communications modules 16, 18 can be, for example, modems or Ethernet cards. The server 10 is connected over the network 14 with a database 30. In certain aspects, the database 30 is a compiled serial image database of tissue healing. In certain aspects, the database 30 is a trained database comprising function quantification post operatively performed with an invasive or non-invasive imaging.

The server 10 includes a processor 20, the communications module 16, and a memory 22. The processor 20 of the server 10 is configured to execute instructions, such as instructions physically coded into the processor 20, instructions received from software in the memory 22, or a combination of both. The processor 20 of the server 10 is configured to perform functions as described herein.

The user device 12 includes a processor 24, the communications module 18, and a memory 26. The processor 24 of the user device 12 is configured to execute instructions, such as instructions physically coded into the processor 24, instructions received from software in the memory 26, or a combination of both. The processor 24 of the user device 12 is configured to perform functions as described herein.

With reference to FIGS. 1 and 2, any imaging (e.g., CT, MM, ECHO (echocardiogram)) capable of producing a 3D image 28 will be the input for the computational algorithm of the server 10. In this simulation, patient imaging (e.g. CT, MM, Echo, 3D Echo, etc.) is first utilized to generate 3D models of the organ/tissue which is the subject of the surgical repair or implantation procedure. Next, off time computer simulations generate a finite number of time deformations of the organ/tissue and any implant device or instrument in response to a pre-determined set of possible surgical steps (e.g., reduce the edge length of a leaflet, or re-locate the leaflets into an artificial root, or move commissural posts in a given direction, or reduce the annulus size by a given amount). The simulation generates the time-deformation of the organ/tissue (4D data) for each possible surgical step.

The scenes generated a priori are unique because each individual scene is a 4D data set (or 5D or more if healing is also modeled), with the ability to represent the time deformation of the tissue being manipulated. These scenes are used as inputs into the novel invented planner, allowing for real-time simulation and functional quantification for planning and decision making. Generation of each scene is accomplished using finite element modeling, reduced order modeling, and other artificial intelligence and machine learning alternatives for modeling. For example, the surgeon would be able to visualize what happens to the entire organ tissue when they constrict a specific patient's annulus. They would then be able to see time deformation of that tissue, as well as an animation of the patient specific tissue responding to the constriction surgical technique (scene 1). Additionally, a second scene would be generated that would (for example) generate an animation of the patient specific tissue responding to the trimming of a leaflet. All the possible steps that are involved in the repair, replacement, or implantation of a device are generated to simulate their corresponding scene.

The scene simulations will also analyze the performance of the post operative organ/tissue system. Functional quantification may include computational fluids modeling, solids modeling with finite element analysis (FEA), computational fluid dynamics modeling (CFD), AI/ML, or reduced order models. The aforementioned models can be trained on a database including functional quantification post operatively performed with an invasive or non-invasive imaging or measurement (e.g., ECHO, cath (catheterization), CT, MM, PET, fMRI (functional magnetic resonance imaging), etc.).

This will be accomplished by allowing the artificial intelligence algorithm to train on a compiled serial image database of tissue healing. Serial images could be obtained using non-invasive or invasive techniques. For applications involving the skin (e.g., plastic surgery) the images could be optical (photographic).

The interactive planner takes all the generated scenes and allows the surgeon to examine the data virtually, interacting between multiple scenes and their corresponding scenarios. All the scenes have been pre-calculated using novel interpolation techniques, allowing the surgeon to see how the entire patient specific organ system changes with each surgical technique. The planner is equipped with augmented reality (AR) and virtual reality (VR) capabilities for an immersive user experience.

Additionally, the ability to visualize multiple treatment scenarios and smoothly navigate the multi-dimensional scenario-space is the desirable feature that will enable data driven surgical planning. The disclosed simulations generate animations of surgical outcomes in a patient according to valve surgery parameters as well as a patient's physiological qualities. A "scenario" in this section will refer to a unique combination of circumstances that differentiate the procedures including but not limited to patient, transcatheter valve type, and anatomical region. Collections of simulated animations that share these contextual variables will be referred to as "sub-scenarios," as they all refer to the same procedure but differ by continuous values controlling outcomes.

Exemplary methods, in accordance with certain aspects of the present disclosure which may be performed by the server 10 and the user device 12, will be described below with reference to FIGS. 3-14D.

A "mesh" in this section refers to a triangulated (or other polygonal structural) set of points providing a 3D representation of CT-scanned geometry.

Figure 3:
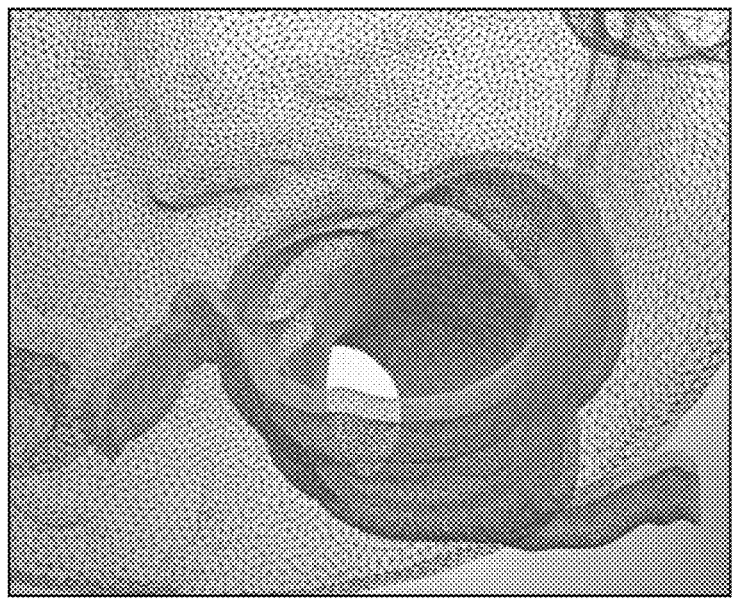
FIG. 3 is an example wireframe rendering looking down through an ascending aorta with no valve, demonstrating the triangulated graph structure of the mesh.

With reference to FIG. 3, this visualization capability is applicable for heart teams planning structural heart procedures, but the visualization of surgical sub-scenarios can be expanded to other surgical specialties such as orthopedic surgery, neurosurgery, neurovascular interventions, plastic and reconstructive surgery and gynecological surgery. The generated scenes do not need to be specific to the cardiovascular system. The novel interpolation techniques generate smoothly going between different 3D files generated from predictive models. The interpolation techniques may be linear, non-linear, or any other technique including reduced order modeling including but not limited to a combination of a pre-determined basis configurations.

Figure 4:
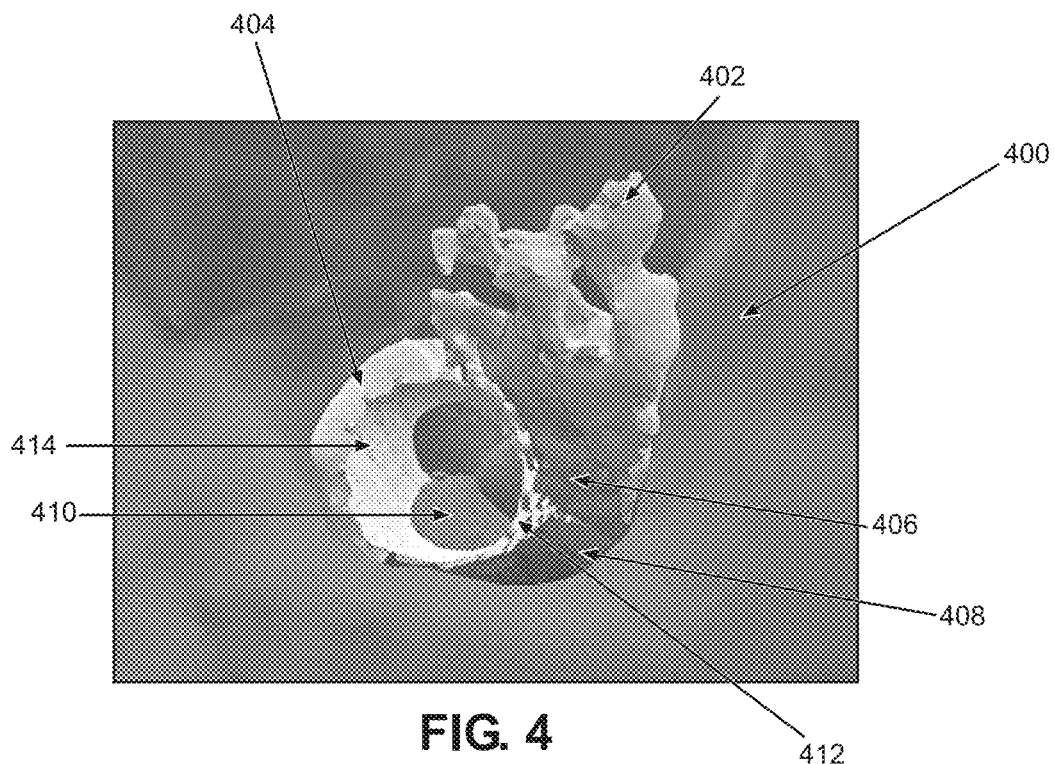
FIG. 4 is an example rendering from same angle as FIG. 3, pushed into the aorta. All zones have been assigned different colors for illustrative purposes. The wall 400 of the aorta is red, calcium 402 is green, each leaflet 404, 406, and 408 of the aorta is yellow, purple, and blue respectively, in this rendering the transcatheter valve leaflets share a zone 410 assigned brown, the stent is composed of two zones 412 and 414, cyan and white.

Referring to FIG. 4, sub-scenarios contain frames of mesh data that can be rendered in sequence to animate procedure outcomes according to that sub-scenario's distinct parameters. Each frame of mesh data contains a set of meshes representing "zones" of a reconstructed 3D volume of a patient's body. For example, zones in a 3D volume containing a patient's ascending aorta could include (1) a section of the aortic wall, (2) the left coronary leaflet, (3) the right coronary leaflet, (4) the non-coronary leaflet of the aortic valve, (5) the transcatheter valve stent.

An example of a scenario is "expansion of an Evolut transcatheter valve inside of an aortic root at 3 mm depth," designed to demonstrate potential blockage of coronary arteries. Sub-scenario parameters for this scenario could include deployment depth, rotation of the valve, etc.

A novel visualizer for viewing simulated outcomes in a way that is accessible, intuitive, and informative requires the following functionalities:
 1. Accurate real-time renderings of simulated data on mobile devices
 2. Smooth transitions between simulated scenarios
 3. Physically-based inspection tools Visualization accuracy of simulated outputs is directly proportional to the complexity of the meshes displayed in the visualizer. Rendering performance is inversely proportional to mesh complexity, and therefore accuracy. This is especially apparent on mobile devices with memory constraints.

Figure 5A:
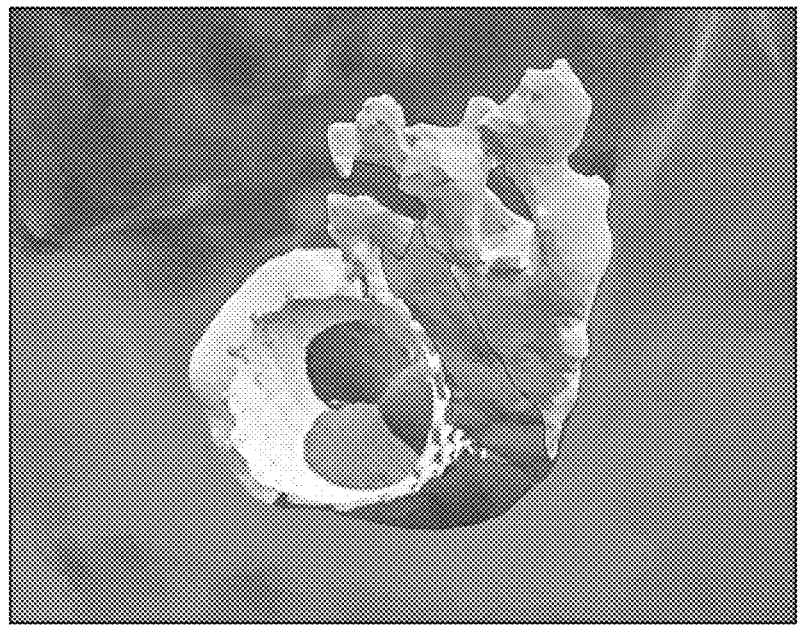
FIG. 5A is an example mesh illustrating a simulated rendering of FIG. 4 at full resolution.

FIG. 5A is an example mesh illustrating a simulated rendering of FIG. 4 at full resolution.

Figure 5B:
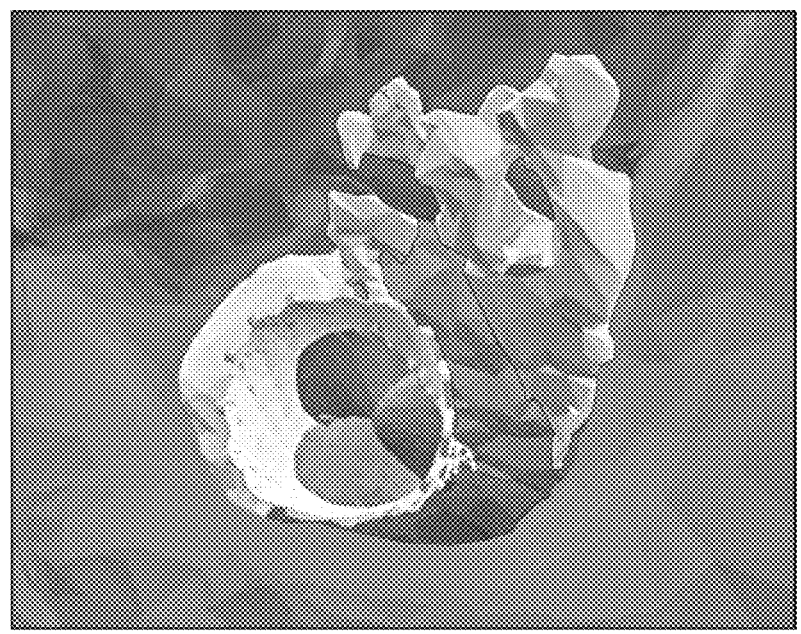
FIG. 5B is an example mesh illustrating a simulated rendering of FIG. 5A after heavy simplification.

FIG. 5B is an example mesh illustrating a simulated rendering of FIG. 5A after heavy simplification. Shape is preserved while the number of vertices and triangles (and therefore the overall data size for mesh storage and transmission) is reduced by around 78%.

Mesh simplification is a tunable algorithm that can help reduce the complexity of meshes without sacrificing significant accuracy by preferring to remove vertices which already fall inside of the plane formed by its immediate neighbors in the mesh. There are many algorithms that can perform this simplification with various tradeoffs.

The disclosed technology, however, requires a more sophisticated approach with a custom solution that selectively preserves original-simulation-level accuracy in more sensitive parts of the simulated output. We can pay this performance cost by simplifying other parts of the simulated output because in many simulations we have large parts of the meshes which remain static across time and aren't as relevant to the physician's decision-making process.

These "areas of high sensitivity" can be determined either manually: a simulation engineer defines axis-aligned bounding boxes containing areas of high sensitivity, or dynamically: an algorithm analyzes groups of simulated outputs to determine which parts are static and finds bounding boxes around those calmer regions.

Figure 6:
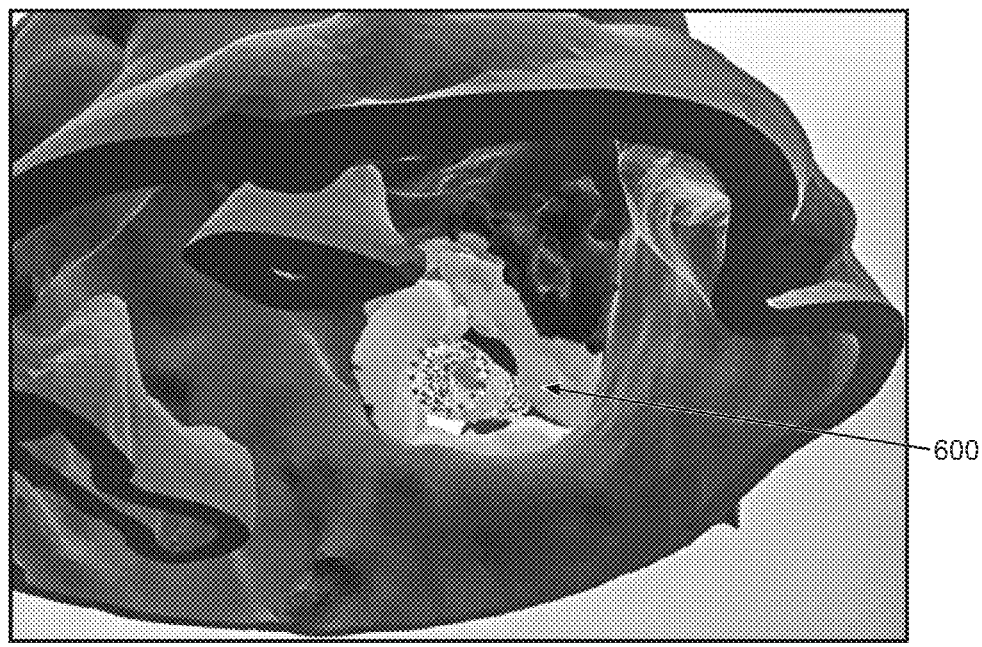
FIG. 6 illustrates regions with high vertex movement 600 (highlighted in red), which correlates directly with areas of high importance when interpreting the results of the simulation.
Figure 7:
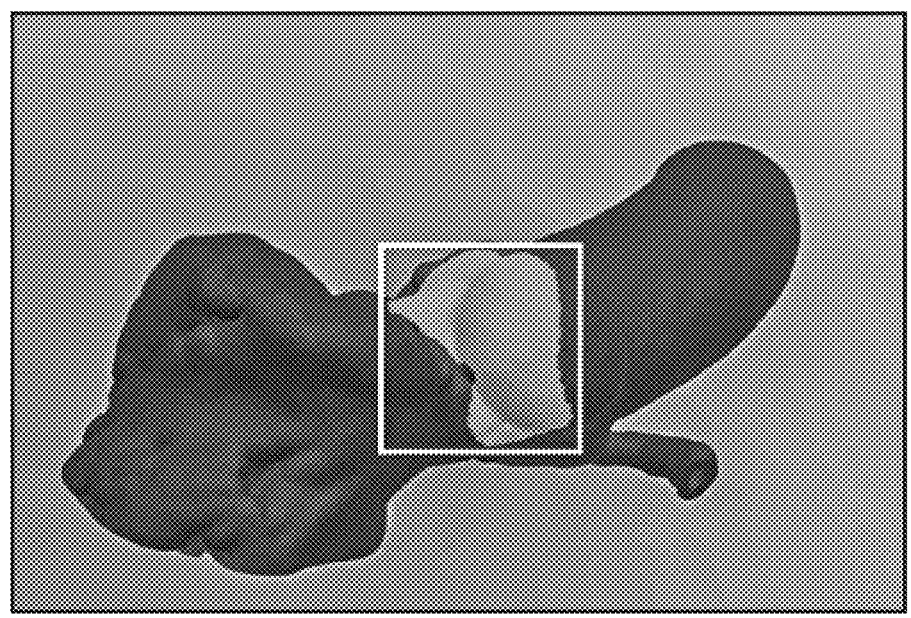
FIG. 7 is an example 2D bounding box drawn on the outside of the aorta showing the area of high sensitivity, the true algorithm uses a 3D axis-aligned bounding box, which the areas of low sensitivity avoid through recursive subdivision.

With reference to FIGS. 6 and 7, in the dynamic case, we find all vertices which do not change position beyond a tunable delta across every frame of every sub-scenario in each scenario, where distance is calculated by a function proportional to Pythagorean length. Note that this algorithm may also use triangle deformation as a heuristic for finding areas of high sensitivity. This means that instead of only looking at raw vertex movement we also consider how far vertices move with respect to their neighbors in the mesh. We then compute an axis-aligned bounding box around these relatively unchanging vertices and recursively divide the bounding box so that its children contain fewer changing vertices until no box contains any changing vertices. The final output is a set of bounding boxes, each containing regions of the mesh that are good candidates for simplification.

Once we have the bounding boxes marking either high or low sensitivity, we divide the original meshes into high and low sensitivity sub-meshes. The low sensitivity sub-meshes are simplified. For increased rendering performance, the low sensitivity sub-meshes can be kept apart and shared between frames and sub-scenarios so that the data is not copied and can be kept in the GPU across multiple frames.

For meshes with additional per-vertex data such as fluid pressure, we either use changes in these values across time as candidates for high-sensitivity identification, or use texture mapping to visually preserve high-frequency features while still reducing the number of vertices, if a loss of accuracy in shape is acceptable so long as data displayed on the surface is not lost.

Figure 8A:
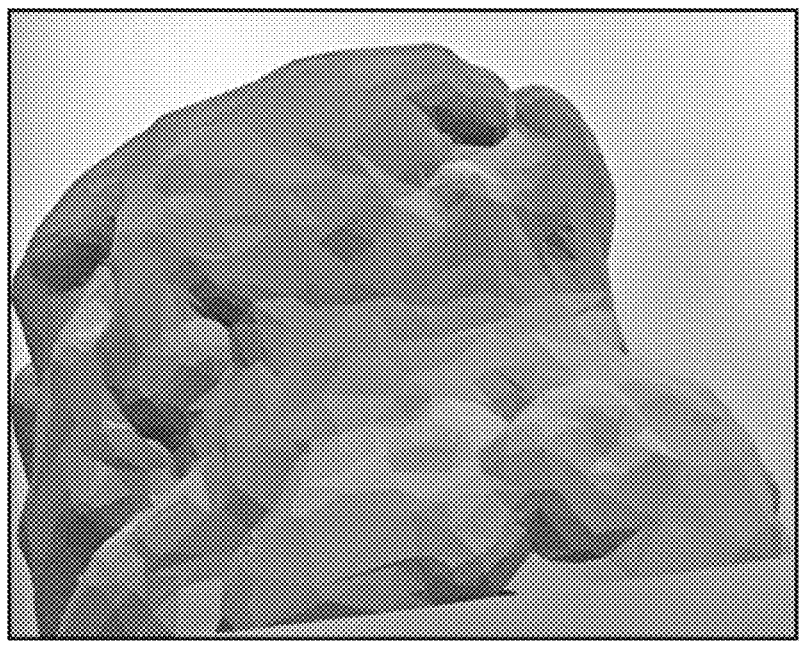
FIG. 8A illustrates part of the aorta rendering without normal data.
Figure 8B:
FIG. 8B illustrates part of the aorta rendering with normal data. The normal data gives the rendering engine information it can use to smooth out lighting, giving the impression of a higher quality model without adding geometric complexity.

Referring to FIGS. 8A and 8B, once the areas of high sensitivity are determined, a well-known mesh simplification algorithm decreases the complexity of the low sensitivity areas to improve rendering performance. We then use other common post-processing algorithms to add per-vertex data such as normals to improve rendering quality by smoothing out lighting at a negligible cost to performance.

In scenarios with sub-scenarios that travel across large parts of the enclosing volume, we employ a level-of-detail system that further optimizes performance by switching between different sets of low-sensitivity areas. This algorithm only computes low sensitivity bounding boxes across animation frames of individual sub-scenarios and tracks the movement of the bounding boxes across the space of sub-scenarios, only combining bounding boxes which are similar by a tunable factor.

Accessibility to data is paramount to a physician's ability to efficiently draw conclusions from the disclosed simulations. We leverage open-source web technologies to make data visualization available on the widest possible range of devices. In certain aspects, GLTF is the mesh description format of choice, as it is easily compressed to preserve bandwidth, it is widely accepted by almost every 3D rendering engine, and it supports the expression of rendering techniques that enable our visualizations to provide compelling depictions of data.

Once mesh data is finalized, we build GLTF representations of the data that can be rendered by any compatible rendering engine. Our construction strategy is described in the next section, as the details are important to our method of interpolation.

The disclosed technology empowers physicians to smoothly navigate different surgical scenarios as a way of encouraging a novel mental model, in which decisions previously seen as static and discrete are expressed as organic potentialities in a continuous space of possibilities.

For a given scenario, we have a set of sub-scenarios that can be charted in this continuous space of possibilities. The axes of this space include time as well as any linearly separable parameters that can be explored for that scenario. To demonstrate continuity across sub-scenarios, the data visualizer generates linear interpolations between sub-scenario meshes.

Figure 9:
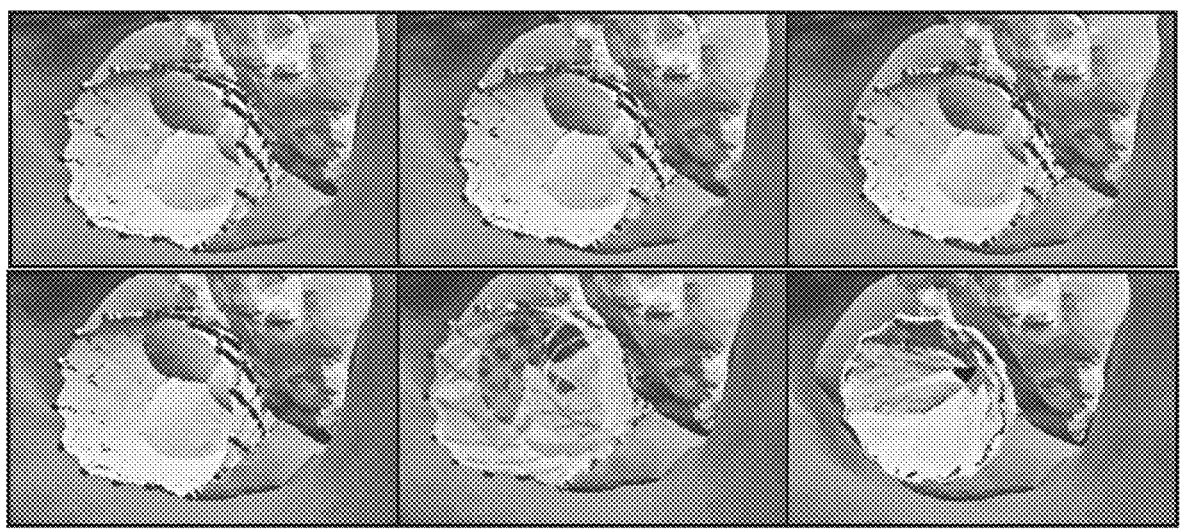
FIG. 9 illustrates example sub-scenarios. The top row examples of FIG. 7 illustrates interpolation between two sub-scenarios (changing valve deployment depth). Because the sub-scenarios share the same triangulation, the vertex data can be smoothly interpolated. The bottom row of FIG. 8 illustrates interpolation between two scenarios (changing the artificial valve brand). Because the different scenarios contain meshes with different triangulations, crossfading is required between the incompatible meshes. Note that because the meshes representing calcium and the aortic root share triangulations across the different scenarios, as the scenarios share the same patient, vertex data for those components of the visualization can still be smoothly interpolated.

Referring to FIG. 9, for meshes to be compatible for interpolation, they must have matching triangulations. A triangulation is a series of indices pointing to vertices that make up a mesh. It is assumed that all sub-scenarios sharing a scenario use the same triangulations, and the mesh simplification explained in the previous section is applied equally to all meshes of each sub-scenario. For interpolation between sub-scenarios that employ the level-of-detail strategy, we use a combination of interpolation and crossfading to give an approximative experience.

Interpolation between meshes is accomplished in the visualizer through a well-known technique called morph targets. Morph targets allow for interpolation between any number of meshes by rendering a weighted average of the positions of their vertices. For interpolation between sub-scenarios containing non-position data we use a similar technique to render a weighted average of color data or textures by computing the average in a custom shader program that runs on the graphics processing unit of the device.

The challenge of smoothly interpolating between an unlimited number of sub-scenarios is maintaining an uninterrupted experience while also downloading and exchanging the significant amounts of data being visualized. The disclosed technology solves this issue by taking maximal advantage of data compression, sharing, streaming, and caching.

Another challenge, which the disclosed technology solves, is determining matching zones for smooth interpolation across variables.

The GLTF files generated from simplified mesh data are compressed using a lossless compression algorithm specifically designed for binary data in the GLTF format. This algorithm yields state-of-the-art compression results that are satisfactory for our use case.

Figure 10:
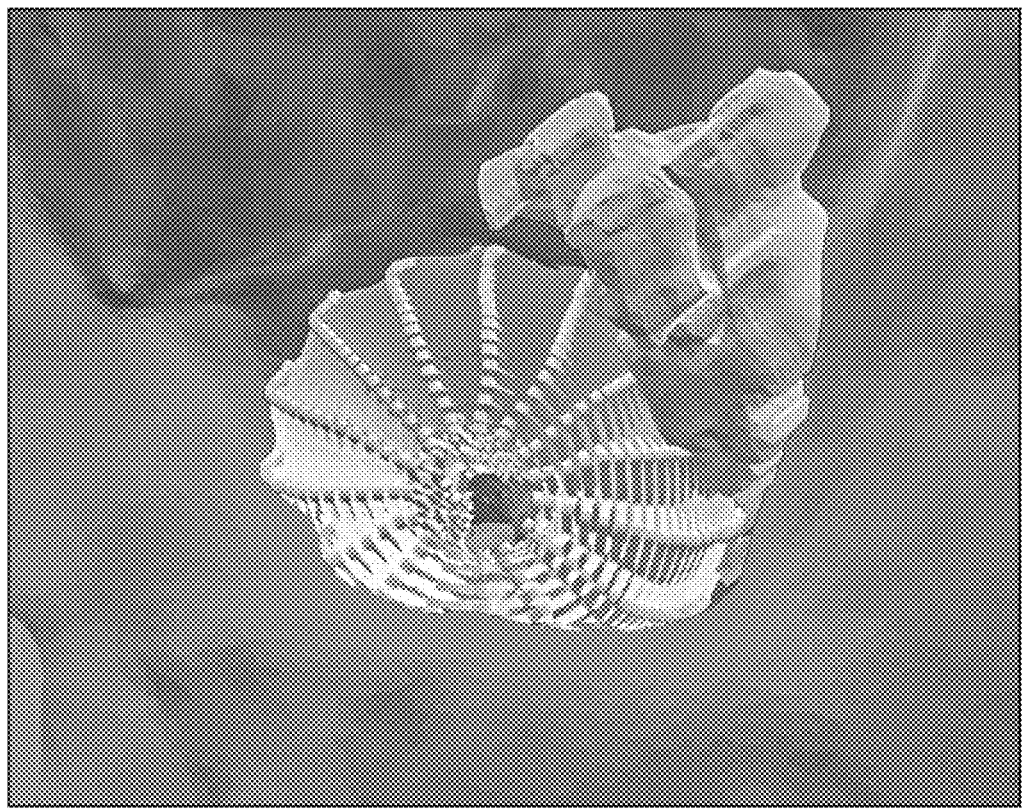
FIG. 10 illustrates a rendering of a GLTF file containing all the animation frames of a sub-scenario, an Evolut transcatheter valve expanding in an aortic root at 1 mm depth.

With reference to FIG. 10, depending on usage metrics, we include in a single GLTF file batches of sub-scenarios that we expect physicians to explore immediately. For example, we can batch sub-scenarios along the time axis so that playing an animation happens immediately once the file containing the sub-scenarios is loaded into memory.

For example, when a physician is inspecting a specific sub-scenario across the time axis, we partially load other sub-scenarios that are nearby in the parameter space so that interpolating to those neighbors happens quickly. Upon navigation to a sub-scenario identified by a different set of parameters, the rest of the frames along the time axis are optionally downloaded, and then decompressed and loaded for visualization. The implementation details of decompression and loading are handled by the rendering engine running the visualization.

Leveraging the bounding boxes from the previous section, we have the option of treating parts of the simulation as completely static. These static components typically serve to contextualize the informative parts of the simulated output and can be treated as separate from the sub-scenarios. In this case we can create a separate GLTF file only containing the static components. If we have dynamic data on the static components that doesn't affect vertex positions, we can have another file only containing that data per sub-scenario so we can still interpolate without incurring the bandwidth cost of downloading copies of vertex data every time the user switches between sub-scenarios.

Figure 11:
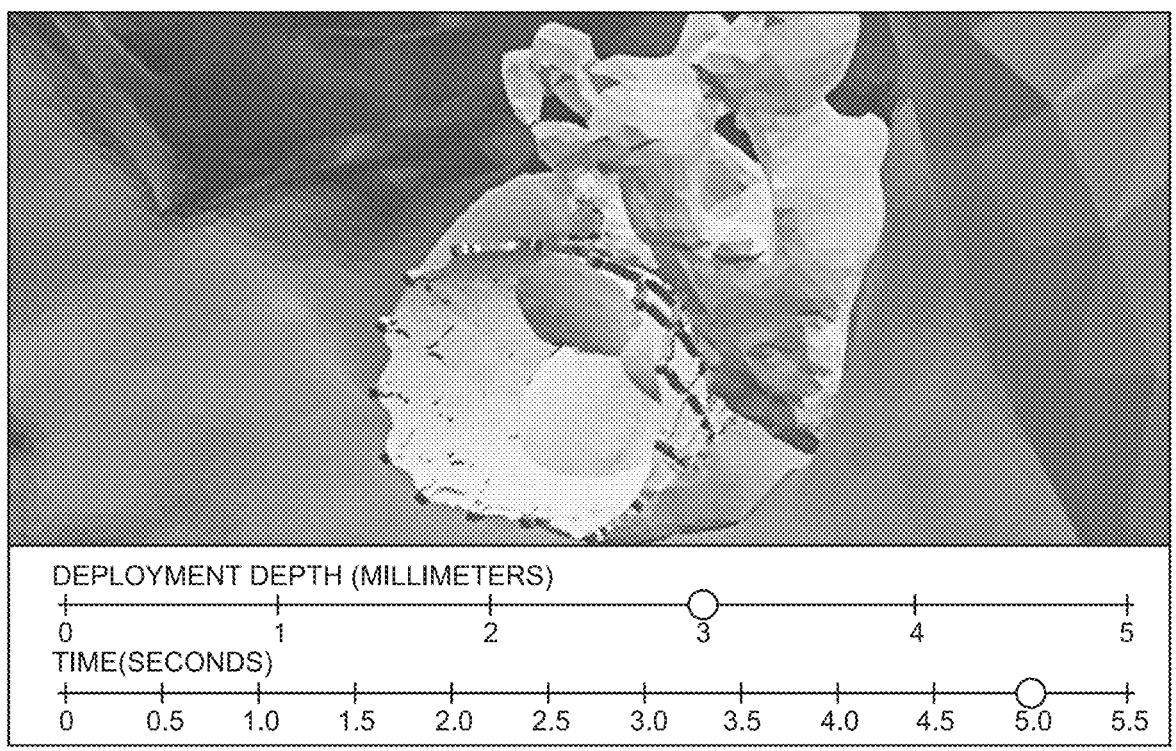
FIG. 11 illustrates an example sliders-based user interface used to control exploration of the parameter space. The vertical lines in the sliders represent explicitly simulated sub-scenarios. Moving the slider thumb between these click stops will drive interpolation between the simulated outputs. The slider thumb magnetically snaps to these click stops so that the physician does not mistakenly observe interpolated output in the planning process.
Figure 12C:
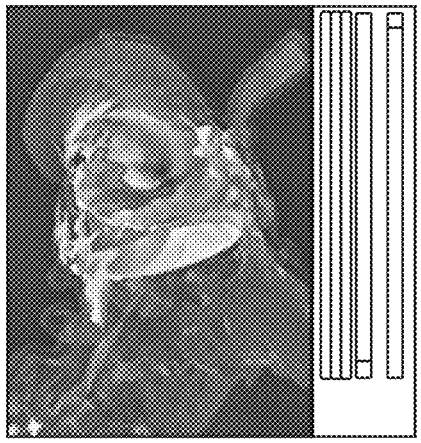
FIGS. 12A-12E illustrate example stretch forces demonstrated on a color gradient, with opacity and redness corresponding to root rupture risk.
Figure 12B:
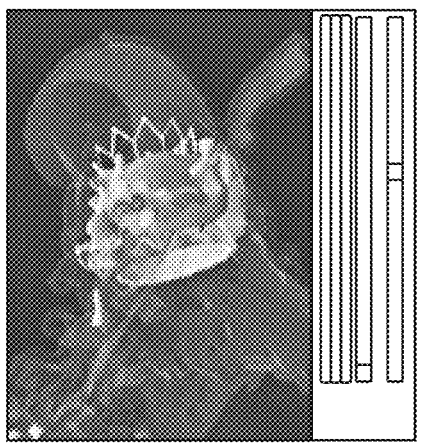
Figure 12E:
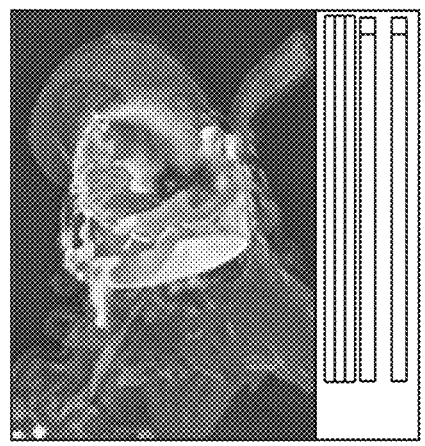
Figure 12A:
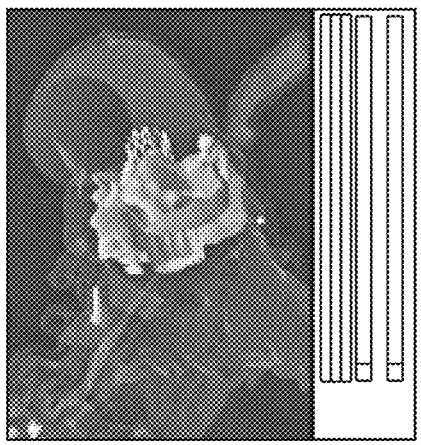
Figure 12D:
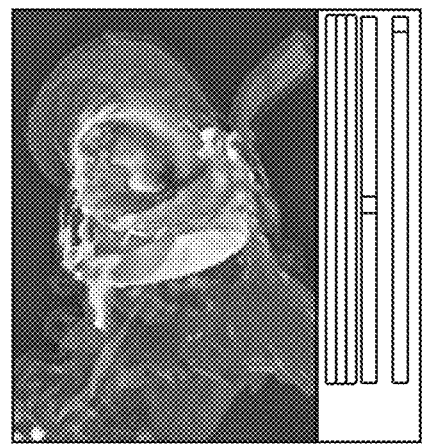
Figure 13:
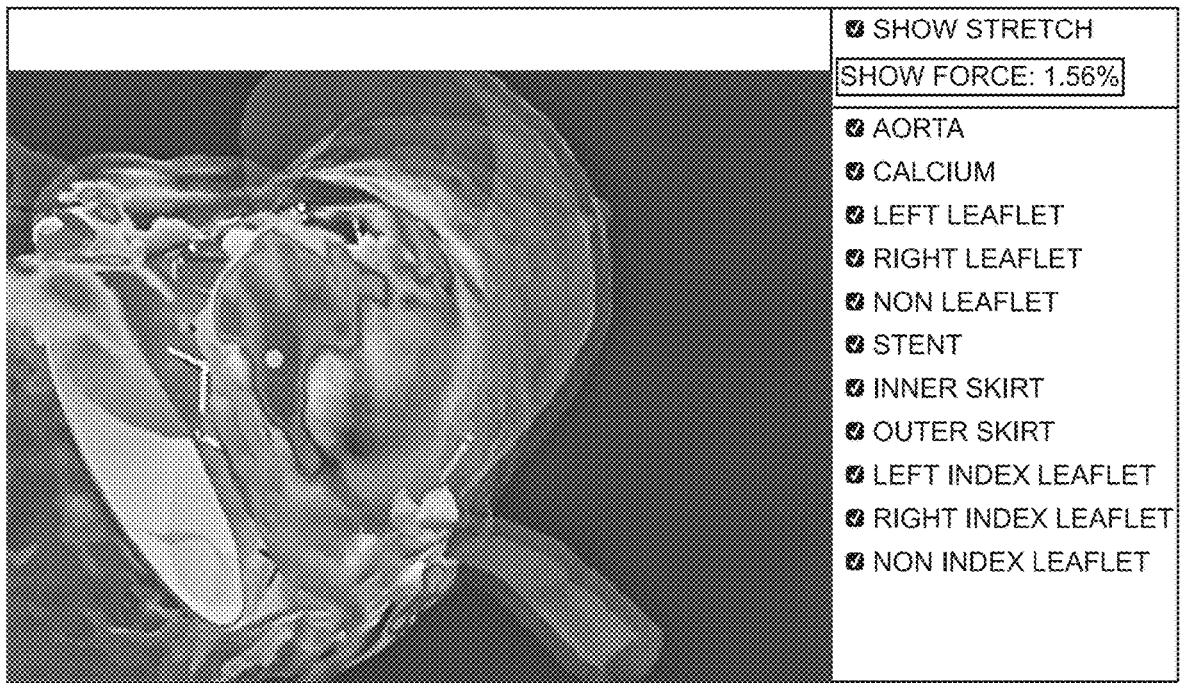
FIG. 13 illustrates a cursor hovering over parts of the simulation, which allows the physician to inspect stretch forces by value directly.
Figure 14:
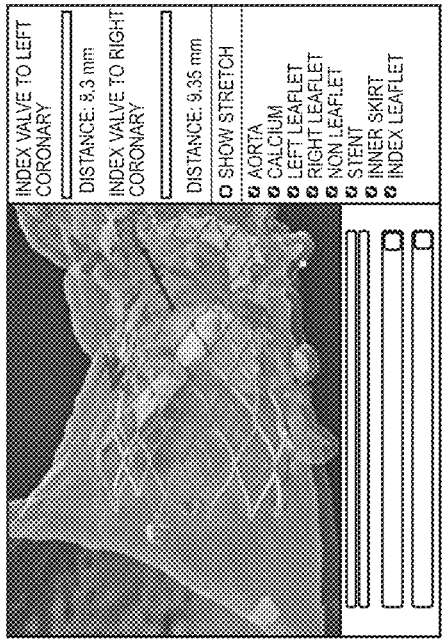
FIGS. 14A-14D illustrate example linear measurements demonstrating the progression of lengths of interest over time and interpolated deployment depth.
Figure 14:
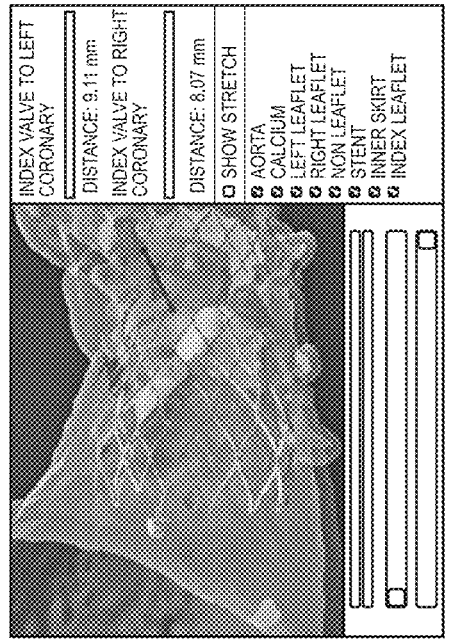
Figure 14:
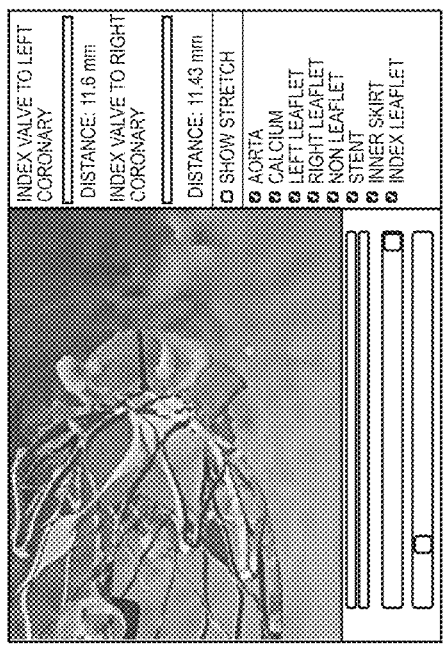
Figure 14:
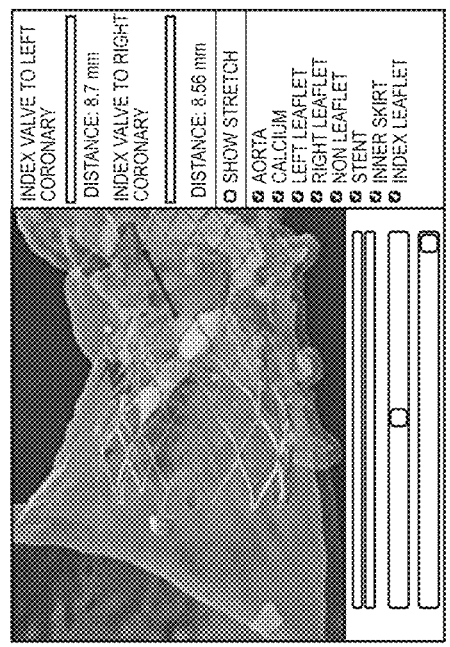

Referring to FIG. 11, with these optimizations, the disclosed technology delivers a smooth experience allowing physicians to understand continuous relationships between parameters they explore. The user interface provided to physicians for exploring sub-scenarios is primarily driven by a set of sliders explaining the set of available parameters. These sliders show the range of simulated sub-scenarios and use click-stops to move the physician to simulated sub-scenarios rather than interpolated ones, as interpolated meshes do not claim medical accuracy.

A visualizer for simulated outputs is useful not only in the abstract sense of catalyzing the synthesis of data into actionable conclusions, but also for grounding simulated data in the real world.

Referring to FIGS. 12A-12E and 14D, the disclosed technology exposes a set of inspection tools that aid physicians in their ability to understand information and present it to others. These tools include but are not limited to per-zone opacity control, per-zone slicing, and measuring tools for stretch forces length, angles, and rate of change in each. These tools allow physicians to collect custom, real-world information from simulated data.

To inspect data and place measurement points, we require real-time raycasting to the mesh. Given the high number of triangles in the mesh, we need to employ a sophisticated approach to determining raycasted positions. Typical raycasting uses a two-step approach, where a simple collider around the mesh is checked for intersection, and then all individual triangles are checked for intersection.

A distinct advantage of mixed reality head-mounted displays (HMD's) is that they offer a highly intuitive sense of scale. Using the visualizer with an HMD will allow for life-size rendering as well as arbitrary scaling. When inspecting simulated outputs in life-size on an augmented reality headset like the Microsoft HoloLens 2, for example, a physician will have physically accurate predictions readily available in the operating room. Because of the disclosed technology's realism in rendering quality, shape, and scale, the physician can conduct a procedure without needing to incur the cognitive load of mapping the visualizer's representation of data to its real-life counterpart.

The surgical planner will provide the surgeon with a detailed virtual plan of the intended procedure. The surgical plan can be provided as input data to a surgical robot to conduct the surgical procedure. By replaying physically accurate simulations of outcomes, the disclosed technology's unique combination of physical measuring tools and interaction patterns in mixed reality will provide physicians with a virtual laboratory in which they can experimentally plan a surgical approach with extremely realistic insights and formulate an optimal surgical plan that is specific to each patient and their anatomy/pathology. This plan can also include any "bail-out" strategies that the surgeon has simulated prior to the surgery in order to plan for emergency lifesaving interventions if they are required.

Figure 15:
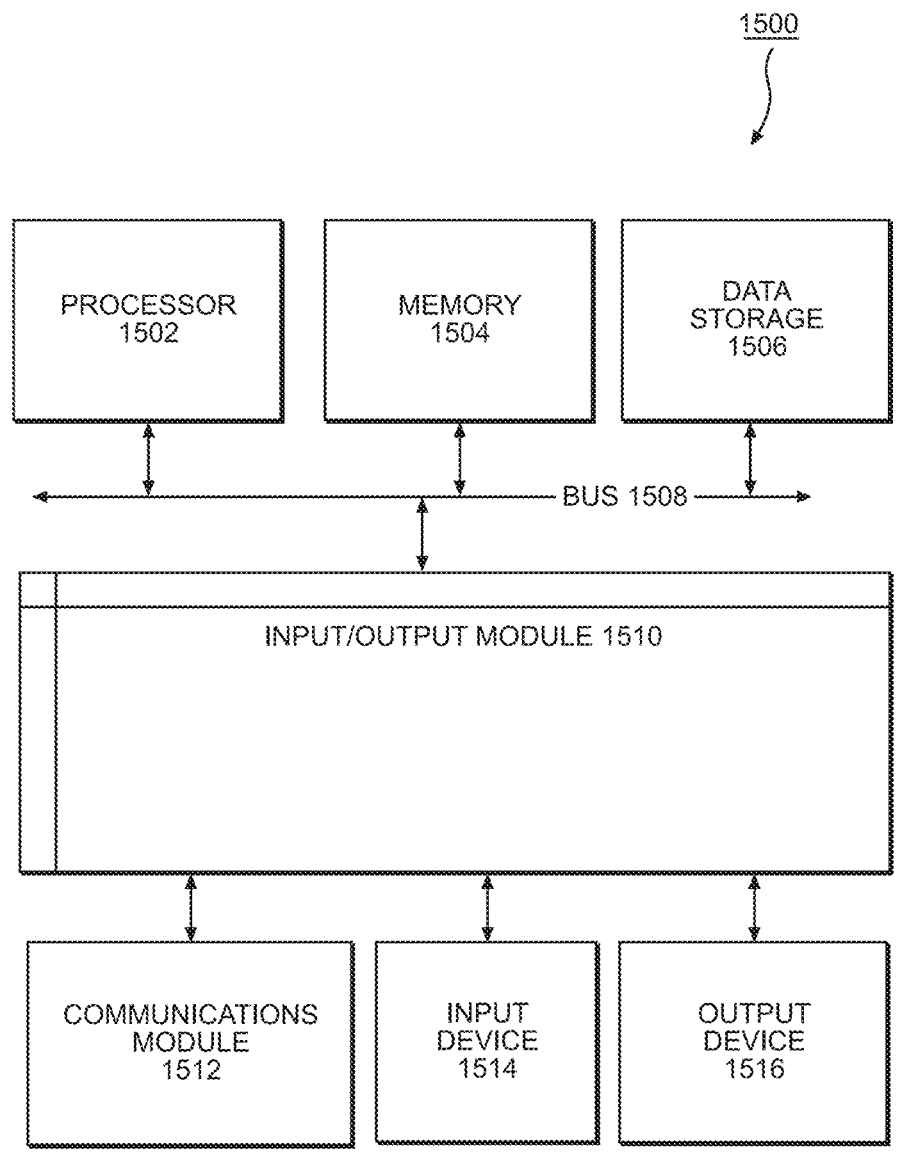
FIG. 15 is a block diagram illustrating an example computer system with which the server and user device of FIG. 1 can be implemented.

FIG. 15 is a block diagram illustrating an example computer system 1500 with which the server 10 and the user device 12 of FIG. 2 can be implemented. In certain aspects, the computer system 1500 may be implemented using hardware or a combination of software and hardware, either in a dedicated server, or integrated into another entity, or distributed across multiple entities.

Computer system 1500 (e.g., the server 10 and the user device 12) includes a bus 1508 or other communication mechanism for communicating information, and a processor 1502 (e.g., the processor 20, 24) coupled with bus 1508 for processing information. According to one aspect, the computer system 1500 can be a cloud computing server of an IaaS that is able to support PaaS and SaaS services.

Computer system 1500 can include, in addition to hardware, code that creates an execution environment for the computer program in question, e.g., code that constitutes processor firmware, a protocol stack, a database management system, an operating system, or a combination of one or more of them stored in an included memory 1504 (e.g., the memory 22, 26), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 1508 for storing information and instructions to be executed by processor 1502. The processor 1502 and the memory 1504 can be supplemented by, or incorporated in, special purpose logic circuitry.

The instructions may be stored in the memory 1504 and implemented in one or more computer program products, e.g., one or more modules of computer program instructions encoded on a computer readable medium for execution by, or to control the operation of, the computer system 1500.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network, such as in a cloud-computing environment. The processes and logic flows described in this specification can be performed by one or more programmable processors executing one or more computer programs to perform functions by operating on input data and generating output.

Computer system 1500 further includes a data storage device 1506 such as a magnetic disk or optical disk, coupled to bus 1508 for storing information and instructions. Computer system 1500 may be coupled via input/output module 1510 to various devices. The input/output module 1510 can be any input/output module. Example input/output modules 1510 include data ports such as USB ports. In addition, input/output module 1510 may be provided in communication with processor 1502, so as to enable near area communication of computer system 1500 with other devices. The input/output module 1510 may provide, for example, for wired communication in some implementations, or for wireless communication in other implementations, and multiple interfaces may also be used. The input/output module 1510 is configured to connect to a communications module 1512. Example communications modules 1512 (e.g., the communications module 16, 18) include networking interface cards, such as Ethernet cards and modems.

In certain aspects, the input/output module 1510 is configured to connect to a plurality of devices, such as an input device 1514 and/or an output device 141516. Example input devices 1514 include a keyboard and a pointing device, e.g., a mouse or a trackball, by which a user can provide input to the computer system 1500. Other kinds of input devices 1514 can be used to provide for interaction with a user as well, such as a tactile input device, visual input device, audio input device, or brain-computer interface device.

According to one aspect of the present disclosure the server 10 and the user device 12 can be implemented using a computer system 1500 in response to processor 1502 executing one or more sequences of one or more instructions contained in memory 1504. Such instructions may be read into memory 1504 from another machine-readable medium, such as data storage device 1506. Execution of the sequences of instructions contained in main memory 1504 causes processor 1502 to perform the process steps described herein. One or more processors in a multi-processing arrangement may also be employed to execute the sequences of instructions contained in memory 1504. Processor 1502 may process the executable instructions and/or data structures by remotely accessing the computer program product, for example by downloading the executable instructions and/or data structures from a remote server through communications module 1512 (e.g., as in a cloud-computing environment). In alternative aspects, hard-wired circuitry may be used in place of or in combination with software instructions to implement various aspects of the present disclosure. Thus, aspects of the present disclosure are not limited to any specific combination of hardware circuitry and software.

Figure 16:
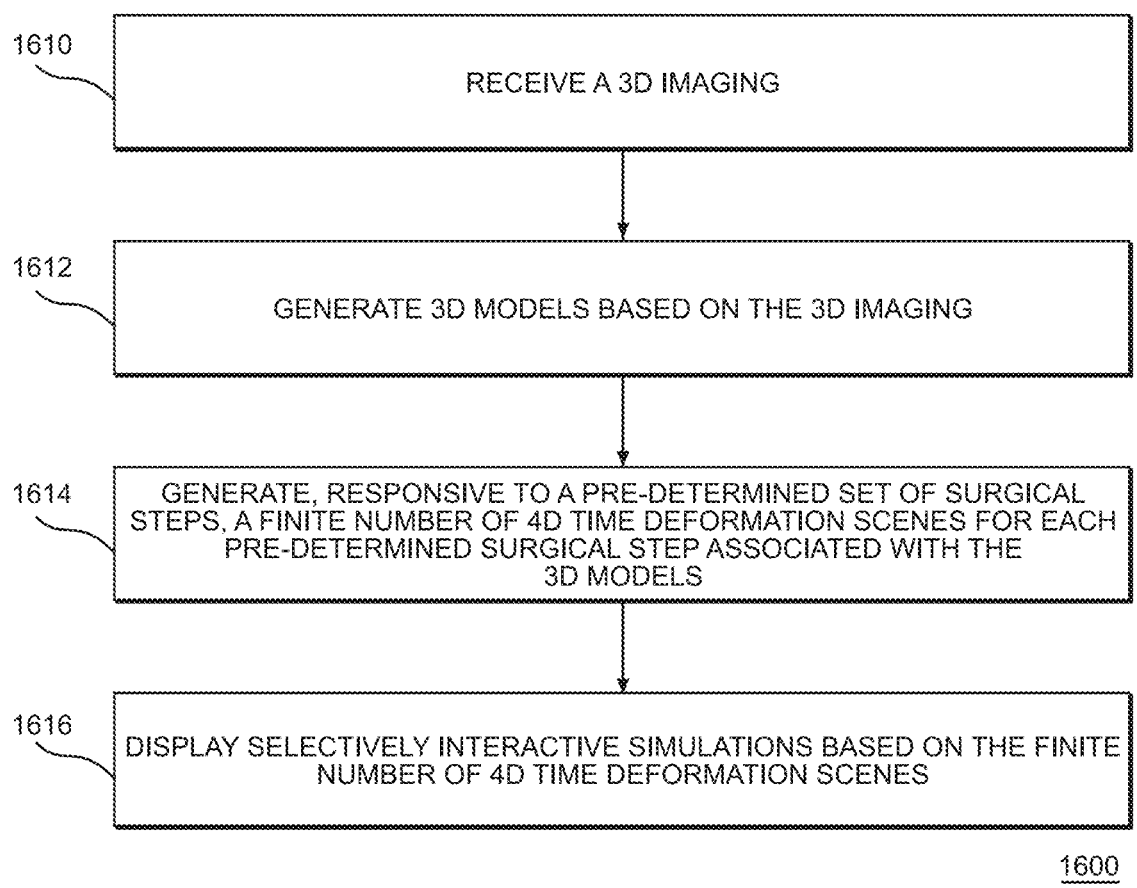
FIG. 16 illustrates an example process for generating integrated interactive simulations of a 3D image.

FIG. 16 illustrates an example process 1600 for generating integrated interactive simulations of a 3D image.

The process begins by proceeding to step 1610 when the processor 20 of the server receives a 3D imaging. As depicted at step 1612, the processor 20 of the server 10 generates 3D models based on the 3D imaging. The processor 20 of the server 10 generates, responsive to a pre-determined set of surgical steps, a finite number of 4D time deformation scenes for each pre-determined surgical step associated with the 3D models, as depicted at step 1614. The processor 20 of the server 10 displays selectively interactive simulations based on the finite number of 4D time deformation scenes, as depicted at step 1616.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. For example, some aspects of the subject matter described in this specification may be performed on a cloud-computing environment. Accordingly, in certain aspects a user of systems and methods as disclosed herein may perform at least some of the steps by accessing a cloud server through a network connection. Further, data files, circuit diagrams, performance specifications and the like resulting from the disclosure may be stored in a database server in the cloud-computing environment, or may be downloaded to a private storage device from the cloud-computing environment.

The term "machine-readable storage medium" or "computer-readable medium" as used herein refers to any medium or media that participates in providing instructions or data to processor 502 for execution. The term "storage medium" as used herein refers to any non-transitory media that store data and/or instructions that cause a machine to operate in a specific fashion. Such a medium may take many forms, including, but not limited to, non-volatile media, volatile media, and transmission media.

As used in this specification of this application, the terms "computer-readable storage medium" and "computer-readable media" are entirely restricted to tangible, physical objects that store information in a form that is readable by a computer. These terms exclude any wireless signals, wired download signals, and any other ephemeral signals. Storage media is distinct from but may be used in conjunction with transmission media. Transmission media participates in transferring information between storage media. For example, transmission media includes coaxial cables, copper wire and fiber optics, including the wires that comprise bus 508. Transmission media can also take the form of acoustic or light waves, such as those generated during radio-wave and infra-red data communications. Furthermore, as used in this specification of this application, the terms "computer", "server", "processor", and "memory" all refer to electronic or other technological devices. These terms exclude people or groups of people. For the purposes of the specification, the terms display or displaying means displaying on an electronic device.

In one aspect, a method may be an operation, an instruction, or a function and vice versa. In one aspect, a clause or a claim may be amended to include some or all of the words (e.g., instructions, operations, functions, or components) recited in either one or more clauses, one or more words, one or more sentences, one or more phrases, one or more paragraphs, and/or one or more claims.

To illustrate the interchangeability of hardware and software, items such as the various illustrative blocks, modules, components, methods, operations, instructions, and algorithms have been described generally in terms of their functionality. Whether such functionality is implemented as hardware, software or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (e.g., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The word "exemplary" is used herein to mean "serving as an example, instance, or illustration." Any embodiment described herein as "exemplary" is not necessarily to be construed as preferred or advantageous over other embodiments. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for".

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A computer-implemented method comprising:
   receiving a 3D imaging;
   generating 3D models based on the 3D imaging;
   generating, responsive to a pre-determined set of surgical steps, a finite number of 4D time deformation scenes for each pre-determined surgical step associated with the 3D models; and
   displaying selectively interactive simulations based on the finite number of 4D time deformation scenes.

2. The computer-implemented method of claim 1, further comprising adjusting the selectively interactive simulations responsive to user input and based on the 3D models.

3. The computer-implemented method of claim 2, further comprising analyzing performance of the selectively interactive simulations that are adjusted.

4. The computer-implemented method of claim 3, wherein analyzing performance of the selectively interactive simulations that are adjusted comprises analyzing with one of computational fluid modeling, solids models with finite element analysis, computational fluid dynamics modeling, artificial intelligence, machine learning and reduced order modeling.

5. The computer-implemented method of claim 4, wherein analyzing performance is based on a trained database comprising function quantification post operatively performed with an one of an invasive and non-invasive imaging.

6. The computer-implemented method of claim 4, wherein analyzing with artificial intelligence comprises training the artificial intelligence on a compiled serial image database of tissue healing.

7. The computer-implemented method of claim 1, wherein generating the finite number of 4D time deformation scenes is performed with artificial intelligence and machine learning modeling.

8. A system comprising:
a memory comprising instructions; and
a processor configured to execute the instructions which, when executed, cause the processor to:
receive a 3D imaging;
generate 3D models based on the 3D imaging;
generate, responsive to a pre-determined set of surgical steps, a finite number of 4D time deformation scenes for each pre-determined surgical step associated with the 3D models; and
display selectively interactive simulations based on the finite number of 4D time deformation scenes.

9. The system of claim 8, further comprising instructions to cause the processor to:
adjust the selectively interactive simulations responsive to user input and based on the 3D models.

10. The system of claim 9, further comprising instructions to cause the processor to:
analyze performance of the selectively interactive simulations that are adjusted.

11. The system of claim 10, wherein the performance of the selectively interactive simulations that are adjusted is analyzed with one of computational fluid modeling, solids models with finite element analysis, computational fluid dynamics modeling, artificial intelligence, machine learning and reduced order modeling.

12. The system of claim 11, wherein the performance of the selectively interactive simulations that are adjusted is analyzed based on a trained database comprising function quantification post operatively performed with one of an invasive and non-invasive imaging.

13. The system of claim 11, wherein the performance of the selectively interactive simulations that are adjusted is analyzed with artificial intelligence comprises training the artificial intelligence on a compiled serial image database of tissue healing.

14. The system of claim 8, wherein the finite number of 4D time deformation scenes is generated with artificial intelligence and machine learning modeling.

15. A non-transitory machine-readable storage medium comprising machine-readable instructions for causing a processor to execute a method, the method comprising:
receiving a 3D imaging;
generating 3D models based on the 3D imaging;
generating, responsive to a pre-determined set of surgical steps, a finite number of 4D time deformation scenes for each pre-determined surgical step associated with the 3D models; and
displaying selectively interactive simulations based on the finite number of 4D time deformation scenes.

16. The non-transitory machine-readable storage medium of claim 15, further including instructions for causing the processor to execute the method comprising:
adjusting the selectively interactive simulations responsive to user input and based on the 3D models.

17. The non-transitory machine-readable storage medium of claim 16, further including instructions for causing the processor to execute the method comprising:
analyzing performance of the selectively interactive simulations that are adjusted.

18. The non-transitory machine-readable storage medium of claim 17, wherein analyzing performance of the selectively interactive simulations that are adjusted comprises analyzing with one of computational fluid modeling, solids models with finite element analysis, computational fluid dynamics modeling, artificial intelligence, machine learning and reduced order modeling.

19. The non-transitory machine-readable storage medium of claim 18, wherein analyzing performance is based on a trained database comprising function quantification post operatively performed with one of an invasive and non-invasive imaging.

20. The non-transitory machine-readable storage medium of claim 18, wherein analyzing with artificial intelligence comprises training the artificial intelligence on a compiled serial image database of tissue healing.

* * * * *